(12) United States Patent
Zhang et al.

(10) Patent No.: US 10,493,056 B2
(45) Date of Patent: Dec. 3, 2019

(54) METHOD OF USE OF DITERPENOID DERIVATIVES AS ANTICANCER AGENTS

(71) Applicant: Hong Kong Baptist University, Hong Kong (HK)

(72) Inventors: Hongjie Zhang, Hong Kong (HK); Man Shing Ricky Wong, Hong Kong (HK); Lei Guo, Hong Kong (HK); Siu Wai Tsang, Hong Kong (HK); Kanglun Liu, Hong Kong (HK); Tongxin Zhang, Hong Kong (HK)

(73) Assignee: Hong Kong Baptist University, Hong Kong (HK)

( * ) Notice: Subject to any disclaimer, the term of this patent is extended or adjusted under 35 U.S.C. 154(b) by 0 days.

(21) Appl. No.: 15/710,842

(22) Filed: Sep. 21, 2017

(65) Prior Publication Data

US 2018/0085344 A1   Mar. 29, 2018

Related U.S. Application Data

(62) Division of application No. 15/277,700, filed on Sep. 27, 2016, now Pat. No. 9,795,589.

(51) Int. Cl.
| | | |
|---|---|---|
| *A61K 31/357* | (2006.01) | |
| *C07D 319/08* | (2006.01) | |
| *C07D 493/08* | (2006.01) | |
| *A61K 31/22* | (2006.01) | |
| *C07C 69/18* | (2006.01) | |

(52) U.S. Cl.
CPC ............ *A61K 31/357* (2013.01); *A61K 31/22* (2013.01); *C07C 69/18* (2013.01); *C07D 319/08* (2013.01); *C07D 493/08* (2013.01); *C07C 2603/86* (2017.05)

(58) Field of Classification Search
CPC ...... C07C 69/18; C07D 319/08; C07D 493/08
See application file for complete search history.

(56) References Cited

PUBLICATIONS

Zhang (Journal of Natural Products; 2002, vol. 65(2)).*
Zhang (Journal of Natural Products; 2002, 65, 215-217).*
International Search Report of PCT/CN2017/103320 dated Dec. 29, 2017.
Guo Lei, et al. Efficient Semisynthesis of (−)-Pseudoirroratin A from (−)-Flexicaulin A and Assessment of Their Antitumor Activities, ACS Medicinal Chemistry Letters, Feb. 28, 2017, vol. 8, No. 3, pp. 372-376.

* cited by examiner

*Primary Examiner* — Pancham Bakshi
(74) *Attorney, Agent, or Firm* — Idea Intellectual Limited; Margaret A. Burke; Sam T. Yip

(57) ABSTRACT

The present invention relates to a group of derivatives synthesized based on the ent-kaurane diterpenoid flexicaulin A and the methods to synthesize such diterpenoid derivatives. In particular, the chemical entities of such synthetic diterpene compounds in the manufacture of a medicament is for the treatment of tumors or cancers.

8 Claims, 6 Drawing Sheets

METHOD OF USE OF DITERPENOID DERIVATIVES AS ANTICANCER AGENTS

CROSS-REFERENCE TO RELATED APPLICATIONS

The present application is a divisional application of the U.S. non-provisional patent application Ser. No. 15/277,700 filed Sep. 27, 2016, and the disclosure of which is incorporated herein by reference in its entirety.

FIELD OF THE INVENTION

The present invention relates to a group of derivatives synthesized based on the ent-kaurane diterpenoid flexicaulin A and the methods to synthesize such diterpenoid derivatives. The invention also relates to the chemical entities of such synthetic diterpene compounds in the manufacture of a medicament for the prevention, treatment, and/or delay in progression of tumors or cancers.

BACKGROUND OF THE INVENTION

Cancer, particularly in the malignant form, is one of the leading causes of death, and accounts for about 13% of all deaths in the world. Although numerous chemotherapeutic approaches are available today, many of them possess narrow therapeutic indices and may exert severe side effects. In addition, chemotherapy resistance is a major concern in the medical management of many cancer patients. Thus, the discovery and development of new and potent anticancer drugs are urgently needed.

Plants are good sources for the discovery and development of anticancer compounds. Paclitaxel and vinblastine are the prime examples of natural compounds that have been extracted as plant alkaloids for cancers. They both exert strong anti-proliferative actions against various types of cancer cells targeting at microtubule cytoskeleton; however, side effects are often accompanied, occurring in more than 30% of patients. Common side effects include low blood counts, hair loss, diarrhea, peripheral neuropathy, nausea, vomiting, arthralgia, myalgia, low blood pressure, unusual bleeding, fatigue, etc. . . . . Nevertheless, drug resistance remains a major obstacle when using paclitaxel and/or vinblastine or other mainstay anticancer agents to treat malignancies.

Over the past decades, a number of pharmacological studies have been focused on the administration of diterpenes, which are a category of plant-derived compounds composed of two terpene units. Terpenes are indeed a group of aromatic organic unsaturated hydrocarbons based on the general formula $(C5H8)_n$. Diterpenes that contain a kaurane skeleton are referred as a class of diterpenoid compounds possessing a tetracyclic or four-membered ring system. The prefix ent- denotes the configurational inversion at all chirality centers; thus, ent-kaurane is an enantiomer of kaurane. Nevertheless, the ent-kaurane diterpenes are often considered as bioactive components. Till now, hundreds to thousands of ent-kaurane diterpenoids isolated from *Isodon* species (Lamiaceae) have been intensively investigated due to their wide range of desirable biological activities including cytotoxic, anti-bacterial and anti-inflammatory effects.

It is an objective of the present invention to provide a group of derivatives synthesized based on the ent-kaurane diterpenoid flexicaulin A for treatment of tumors or cancers and the methods to synthesize such diterpenoid derivatives.

Citation or identification of any reference in this section or any other section of this application shall not be construed as an admission that such reference is available as prior art for the present application.

SUMMARY OF THE INVENTION

Accordingly, the objective of this invention relates to a diterpene compound based on formula (I), formula (II), formula (III), or formula (IV), the derivatives or chemical variants thereof, and/or a pharmaceutically acceptable salt or pro-drug thereof, either alone or in combination with one or more of other pharmaceutically acceptable anticancer agent(s) in a pharmaceutical formulation, for use in the treatment or delay of progression of a tumor or cancer in a patient. It also relates to the use of a combination of one or more of said diterpene compound(s) as clinical antitumor or anticancer agent(s), particularly in treatment or delay of progression of a cancer in a patient. It further relates to the use of an extract or a fraction made from plant material or extraction material containing one or more compound(s) for use in treatment or delay of progression of a cancer in a patient:

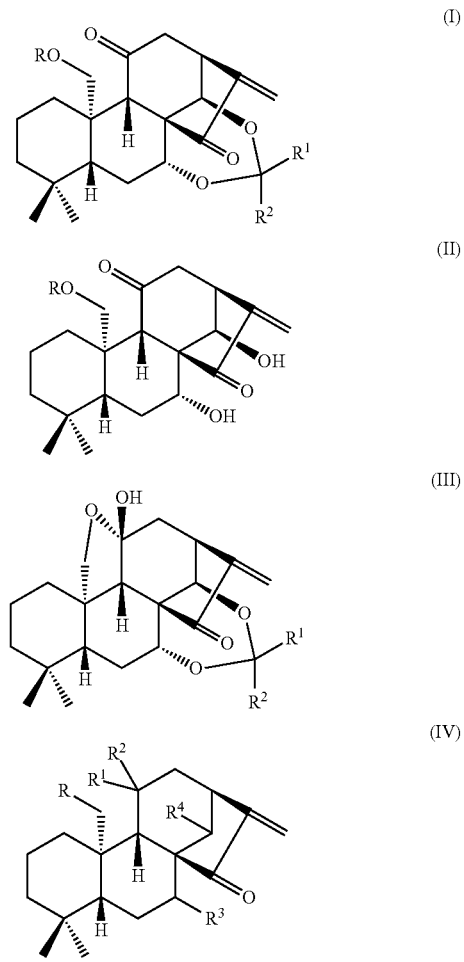

In a first aspect of the present invention, there is provided a compound of formula (IV):

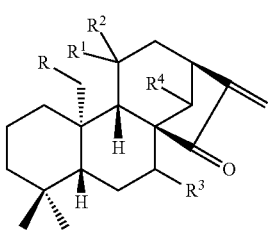

(IV)

wherein $R^1$ and $R^2$ are taken together with the carbon atom to which they are attached to form a carboxyl groups (C=O); or while one of $R^1$ and $R^2$ is hydroxyl group, $R^3$ and $R^4$ are taken together with the carbon atoms to which they are attached to form a heterocyclyl group, and R and the other one of $R^1$ and $R^2$ are taken together with the carbon atoms to which they are attached to form a heterocyclyl group;

while R is selected from —$OR^5$ and —$OC(O)R^5$, $R^3$ and $R^4$ are taken together with the carbon atoms to which they are attached to form a heterocyclyl group optionally substituted with 1, 2, 3, 4 or 5 $R^6$; or while R is selected from —$OR^7$ and —$C(O)R^7$, $R^1$ and $R^2$ are taken together with the carbon atoms to which they are attached to form a carboxyl groups (C=O), and $R^3$ and $R^4$ are both hydroxyl groups;

$R^5$ is independently hydrogen or selected from hydrocarbyl and heterocyclyl, either of which is optionally substituted with 1, 2, 3, 4 or 5 $R^8$;

$R^6$ is independently selected from hydrogen, halogen, trifluoromethyl, cyano, nitro, hydrocarbyl optionally substituted with 1, 2, 3, 4 or 5 $R^8$, heterocyclyl optionally substituted with 1, 2, 3, 4 or 5 $R^8$, —$OR^9$, —$C(O)R^{10}$, —$C(O)N(R^9)R^{10}$, —$C(O)OR^9$, —$OC(O)R^9$, —$S(O)_2R^9$, —$S(O)_2N(R^9)R^{10}$, and —$N(R^9)R^{10}$;

$R^7$ is selected from hydrocarbyl and heterocyclyl, either of which is optionally substituted with 1, 2, 3, 4 or 5 $R^8$;

$R^8$ is independently selected from halogen, trifluoromethyl, cyano, nitro, oxo, —$OR^9$, —$C(O)R^{10}$, —$C(O)N(R^9)R^{10}$, —$C(O)OR^9$, —$OC(O)R^{10}$, —$S(O)_2R^9$, —$S(O)_2N(R^9)R^{10}$, —$N(R^9)R^{10}$;

$R^9$ and $R^{19}$ are each independently hydrogen or selected from hydrocarbyl and heterocyclyl, either of which is optionally substituted with 1, 2, 3, 4 or 5 substituents independently selected from halogen, cyano, amino, hydroxy, $C_{1-6}$ alkyl and $C_{1-6}$ alkoxy;

or an enantiomer thereof;

or a pharmaceutically acceptable salt or prodrug thereof.

In a first embodiment of the first aspect of the present invention, there is provided a compound of formula (IV) wherein said compound is an optically pure stereoisomer.

In a second embodiment of the first aspect of the present invention, there is provided a compound of formula (IV) wherein said compound is an enantiomer.

In a third embodiment of the first aspect of the present invention, there is provided a compound of formula (IV) wherein said compound is a racemate.

In a fourth embodiment of the first aspect of the present invention, there is provided a compound of formula (IV) wherein said compound is a diastereomer.

In a fifth embodiment of the first aspect of the present invention, a pharmaceutical composition comprising an effective amount of the compound of formula (IV) and a pharmaceutically acceptable carrier thereof.

In a sixth embodiment of the first aspect of the present invention, there is provided a compound of formula (IV) wherein said compound is selected from FA2, FA3, or FA4 with the following formulae respectively:

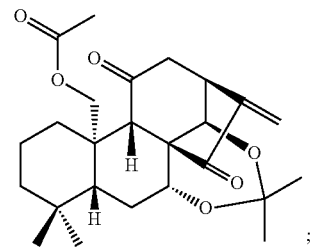

FA2

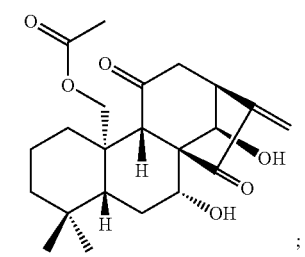

FA3

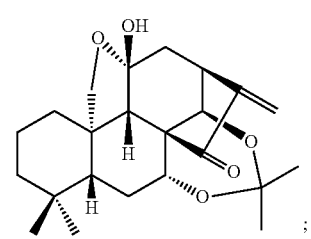

FA4 or a pharmaceutically acceptable salt or prodrug thereof.

In a second aspect of the present invention there is provided a method of using the compound of formula (IV) and/or the derivatives or chemical variants thereof and/or in combination with one or more of other pharmaceutically acceptable anticancer agent(s) in treatment, prevention and/or delay of progression of a cancer in a subject in need thereof.

In a first embodiment of the second aspect of the present invention there is provide a method of using the compound of formula (IV) and/or the derivatives or chemical variants thereof and/or in combination with one or more of other pharmaceutically acceptable anticancer agent(s) in treatment, prevention or delay of progression of a cancer wherein said subject is a human.

In a second embodiment of the second aspect of the present invention there is provide a method of using the compound of formula (IV) and/or the derivatives or chemical variants thereof and/or in combination with one or more of other pharmaceutically acceptable anticancer agent(s) in treatment, prevention or delay of progression of a cancer wherein said cancer comprises colon cancer, breast cancer, prostate cancer, lung cancer, oral epidermoid cancer and melanoma cancer.

In a third aspect of the present invention there is provide a method of treating and preventing development and progression of a cancer comprising administering the compound of formula (IV) to a subject in need thereof, wherein said cancer comprises colon cancer, breast cancer, prostate cancer, lung cancer, oral epidermoid cancer and melanoma cancer.

In a first embodiment of the third aspect of the present invention there is provided a method of treating and preventing development and progression of a cancer comprising administering the compound of formula (IV) wherein said subject is a human.

In a fourth aspect of the present invention there is provided a compound according to the formula (I), formula (II), or formula (III):

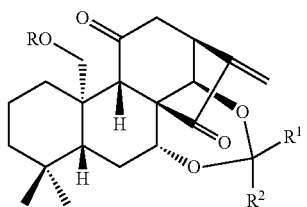

(I)

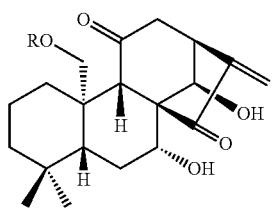

(II)

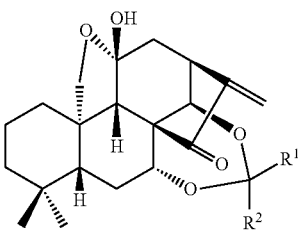

(III)

wherein $R^1$ and $R^2$ are each independently selected from hydrogen, halogen, alkoxy, hydrocarbyl optionally substituted with 1, 2, 3, 4 or 5 $R^3$, or heterocyclyl optionally substituted with 1, 2, 3, 4 or 5 $R^3$;

$R^3$ is independently selected from hydrogen, halogen, trifluoromethyl, cyano, nitro, hydrocarbyl optionally substituted with 1, 2, 3, 4 or 5 $R^4$, heterocyclyl optionally substituted with 1, 2, 3, 4 or 5 $R^4$, —$OR^5$, —$C(O)R^6$, —$C(O)N(R^5)R^6$, —$C(O)OR^5$, —$OC(O)R^5$, —$S(O)_2R^5$, —$S(O)_2N(R^5)R^6$, and —$N(R^5)R^6$;

$R^4$ is independently selected from halogen, trifluoromethyl, cyano, nitro, oxo, —$OR^5$, —$C(O)R^6$, —$C(O)N(R^5)R^6$, —$C(O)OR^5$, —$OC(O)R^6$, —$S(O)_2R^5$, —$S(O)_2N(R^5)R^6$, —$N(R^5)R^6$;

$R^5$ and $R^6$ are each independently hydrogen or selected from hydrocarbyl and heterocyclyl, either of which is optionally substituted with 1, 2, 3, 4 or 5 substituents independently selected from halogen, cyano, amino, hydroxy, $C_{1-6}$ alkyl and $C_{1-6}$ alkoxy;

R is selected from $R^7$ and $(C=O)R^7$;

$R^7$ according to formula (I) is independently selected from hydrogen and hydrocarbyl optionally substituted with 1, 2, 3, 4 or 5 substituents independently selected from halogen, cyano, amino, hydroxy, $C_{1-6}$ alkyl and $C_{1-6}$ alkoxy, while $R^7$ according to formula (II) is hydrocarbyl optionally substituted with 1, 2, 3, 4 or 5 substituents independently selected from halogen, cyano, amino, hydroxy, $C_{1-6}$ alkyl and $C_{1-6}$ alkoxy, meaning that R is not hydrogen atom in formula (II);

or an enantiomer thereof;

or a pharmaceutically acceptable salt or prodrug thereof.

In a first embodiment of the fourth aspect of the present invention, there is provided a compound of formula (I), (II) or (III) wherein said compound is an optically pure stereoisomer.

In a second embodiment of the fourth aspect of the present invention, there is provided a compound of formula (I), (II) or (III) wherein said compound is an enantiomer.

In a third embodiment of the fourth aspect of the present invention, there is provided a compound of formula (I), (II) or (III) wherein said compound is a racemate.

In a fourth embodiment of the fourth aspect of the present invention, there is provided a compound of formula (I), (II) or (III) wherein said compound is a diastereomer.

In a fifth embodiment of the fourth aspect of the present invention, a pharmaceutical composition comprising an effective amount of the compound of formula (I), (II) or (III), and a pharmaceutically acceptable carrier thereof In a sixth embodiment of the fourth aspect of the present invention, there is provided a compound of formula (I), (II) or (III) wherein said compound is selected from FA2, FA3, or FA4 with the following formulae respectively:

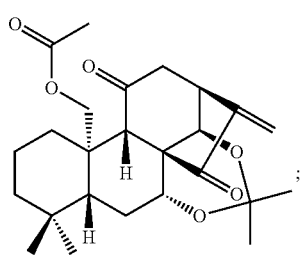

FA2

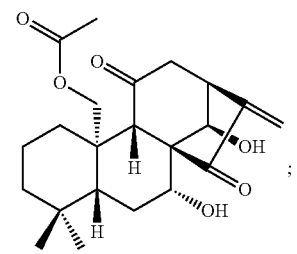

FA3

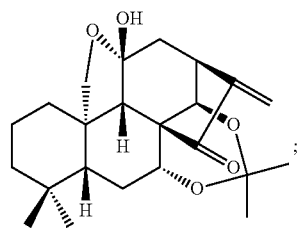

FA4 or a pharmaceutically acceptable salt or prodrug thereof.

In a fifth aspect of the present invention there is provided a method of using the compound of formula (I), (II) or (III), and/or the derivatives or chemical variants thereof and/or in combination with one or more of other pharmaceutically acceptable anticancer agent(s) in treatment, prevention and/or delay of progression of a cancer in a subject in need thereof.

In a first embodiment of the fifth aspect of the present invention there is provide a method of using the compound of formula (I), (II) or (III) and/or the derivatives or chemical variants thereof and/or in combination with one or more of other pharmaceutically acceptable anticancer agent(s) in treatment, prevention or delay of progression of a cancer wherein said subject is a human.

In a second embodiment of the fifth aspect of the present invention there is provide a method of using the compound of formula (I), (II) or (III) and/or the derivatives or chemical variants thereof and/or in combination with one or more of other pharmaceutically acceptable anticancer agent(s) in treatment, prevention or delay of progression of a cancer wherein said cancer comprises colon cancer, breast cancer, prostate cancer, lung cancer, oral epidermoid cancer and melanoma cancer.

In a sixth aspect of the present invention there is provide a method of treating and preventing development and progression of a cancer comprising administering the compound of formula (I), (II) or (III) to a subject in need thereof, wherein said cancer comprises colon cancer, breast cancer, prostate cancer, lung cancer, oral epidermoid cancer and melanoma cancer.

In a seventh aspect of the present invention, there is provided a method of synthesizing a compound of formula FA1, FA2, FA3, or FA4, or Psedoirroratin A (PA) from Flexicaulin A (FA) comprising the following synthesis schemes:

Scheme 1:

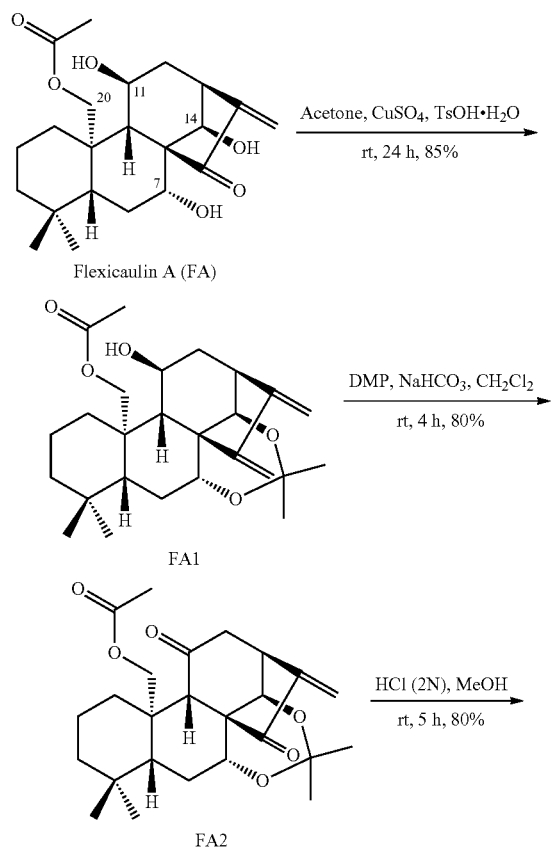

Scheme 2:

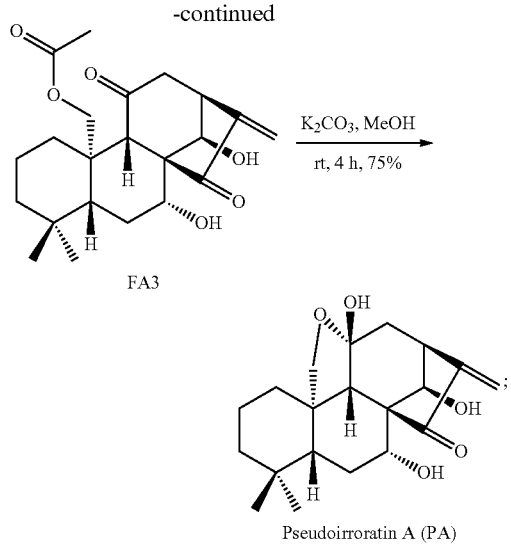

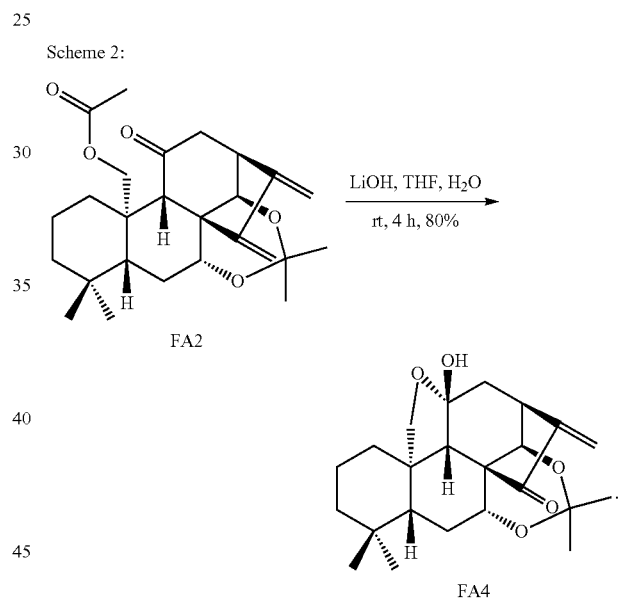

In a first embodiment of the seventh aspect of the present invention, wherein under said synthesis scheme 1, said FA1 is synthesized from the following steps:
a) adding a solution of flexicaulin A (FA, 110 mg, 0.28 mmol) into an anhydrous acetone (12 mL) with anhydrous $CuSO_4$ (447 mg, 2.8 mmol) and catalyzed $TsOH \cdot H_2O$ (5 mg) to form a mixture;
b) stirring the mixture for 24 hours at room temperature under $N_2$ protection,
c) alkalifying the mixture with $Et_3N$ (0.5 ml) and filtering through Celite to afford a clear solution;
d) washing Celite with Ethyl acetate and combining the clear solution with the organic phase previously separated before being dried with anhydrous $Na_2SO_4$
e) evaporating residual solvent from said combination of clear solution and organic phase; and
f) purifying residue by silica gel chromatography using petroleum ether and ethyl acetate at 1:1 ratio as eluent to afford 109 mg white solid of FA1 in 90% yield.

In a second embodiment of the seventh aspect of the present invention, wherein under said synthesis scheme 1, said FA2 is synthesized from the following steps:
a) adding a solution of FA1 (84.5 mg, 0.2 mmol) in $CH_2Cl_2$ (20 mL) with DMP.3AcOH (254 mg, 0.6 mmol) and $NaHCO_3$ (168 mg, 2.0 mmol) in an ice-water bath to form a mixture;
b) stirring the mixture overnight at room temperature under $N_2$ protection;
c) filtering the mixture through Celite followed by washing with $CH_2Cl_2$ and being dried with anhydrous $Na_2SO_4$
d) removing solvent from the mixture; and
e) purifying residue by silica gel chromatography using petroleum ether and ethyl acetate 3:1 ratio as eluent to afford 73 mg white solid of FA2 in 85% yield.

In a third embodiment of the seventh aspect of the present invention, wherein under said synthesis scheme 1, said FA3 is synthesized from the following steps:
a) adding a solution of FA2 (90 mg, 0.21 mmol) in MeOH (25 mL) dropwise with 2N HCl (1 ml, Con. HCl diluted in MeOH) and $H_2O$ (0.5 ml) at room temperature to form a mixture followed by stirring overnight;
b) evaporating solvent from the mixture;
c) purifying residue by silica gel chromatography using petroleum ether and ethyl acetate 1:1 ratio as eluent to afford 68 mg white solid of FA3 in 84% yield.

In a fourth embodiment of the seventh aspect of the present invention, wherein under said synthesis scheme 1, said PA is synthesized from the following steps:
a) adding a solution of FA3 (15 mg, 0.038 mmol) in THF (16 mL) dropwise with an aqueous solution of LiOH (1 ml, 0.12 M) at a room temperature to form a mixture followed by stirring overnight under $N_2$ protection;
b) until the mixture is changed into yellow, quenching the mixture with water and extracting an organic phase with ethyl acetate;
c) combining the organic phase with the aqueous phase before being dried with $Na_2SO_4$ and evaporated in vacuum; and
d) purifying residue by silica gel chromatography using petroleum ether and ethyl acetate 1:1 ratio as eluent to afford 6 mg white solid of PA in 45% yield.

In an eighth aspect of the present invention, an active pharmaceutical ingredient (API) for use or preparation in a pharmaceutical composition for preventing, treating, and/or delaying progression of tumors or cancers in a subject in need thereof which is synthesized according to the method of synthesis as described herein is provided.

Those skilled in the art will appreciate that the invention described herein is susceptible to variations and modifications other than those specifically described.

The invention includes all such variation and modifications. The invention also includes all of the steps and features referred to or indicated in the specification, individually or collectively and any and all combinations or any two or more of the steps or features.

Throughout this specification, unless the context requires otherwise, the word "comprise" or variations such as "comprises" or "comprising", will be understood to imply the inclusion of a stated integer or group of integers but not the exclusion of any other integer or group of integers. It is also noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

Furthermore, throughout the specification and claims, unless the context requires otherwise, the word "include" or variations such as "includes" or "including", will be understood to imply the inclusion of a stated integer or group of integers but not the exclusion of any other integer or group of integers.

In the method of synthesis of any of the compounds described herein, the steps can be carried out in any order without departing from the principles of the invention, except when a temporal or operational sequence is explicitly recited. Recitation in a claim to the effect that first a step is performed, and then several other steps are subsequently performed, shall be taken to mean that the first step is performed before any of the other steps, but the other steps can be performed in any suitable sequence, unless a sequence is further recited within the other steps. For example, claim elements that recite "Step A, Step B, Step C, Step D, and Step E" shall be construed to mean step A is carried out first, step E is carried out last, and steps B, C, and D can be carried out in any sequence between steps A and E, and that the sequence still falls within the literal scope of the claimed process. A given step or sub-set of steps can also be repeated.

Furthermore, specified steps can be carried out concurrently unless explicit claim language recites that they be carried out separately. For example, a claimed step of doing X and a claimed step of doing Y can be conducted simultaneously within a single operation, and the resulting process will fall within the literal scope of the claimed process.

Other definitions for selected terms used herein may be found within the detailed description of the invention and apply throughout. Unless otherwise defined, all other technical terms used herein have the same meaning as commonly understood to one of ordinary skill in the art to which the invention belongs.

Other aspects and advantages of the invention will be apparent to those skilled in the art from a review of the ensuing description.

BRIEF DESCRIPTION OF THE DRAWINGS

The above and other objects and features of the present invention will become apparent from the following description of the invention, when taken in conjunction with the accompanying drawings, in which.

DETAILED DESCRIPTION OF THE INVENTION

Figure 1:
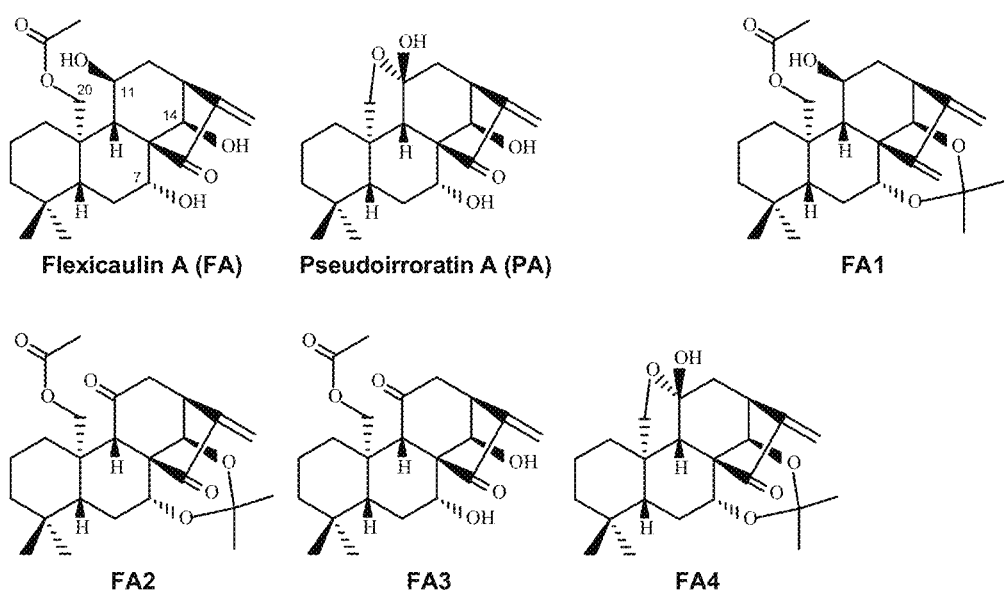
FIG. 1 shows the chemical structures of flexicaulin A (FA), pseudoirroratin A (PA), FA1, FA2, FA3 and FA4.

The present invention is not to be limited in scope by any of the specific embodiments described herein. The following embodiments are presented for exemplification only.

Definitions

Diterpene or Diterpenoid

The term "diterpene" or "diterpenoid" refers to a compound with the fixed skeleton containing 20 carbons, and being formed from geranylgeranyl diphosphate (GGPP). Example of diterpenes include ent-kaurenes.

Kaurene, Kaurane and Kaurenoid

The term "kaurene", "kaurane" or "kaurenoid" refers to a compound comprising the basic structure shown as below. The structure skeleton has a 4-ring system fused with 6:6:6:5 member rings. The rings A and B are trans-fused at C-5 and C-10. The rings B and C are cis-fused at C-8 and C-9. The fourth ring (ring D) is a five-member ring, which is fused with ring C at C-8 and C-13. The four rings are substituted with four methyl groups with two being substituted at C-4, one being substituted at C-10 and one being substituted at C-16.

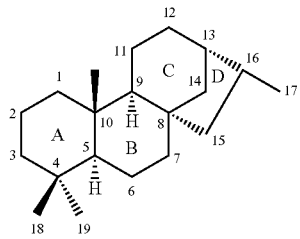

Kaurene or Kaurane or Kaurenoid ent-Kaurene, ent-Kaurane and ent-Kaurenoid

The term "ent-kaurene", "ent-kaurane" or "ent-kaurenoid" is an enantiomer of a kaurene, kaurane or kaurenoid. They refer to a compound comprising the basic structure skeleton shown as below.

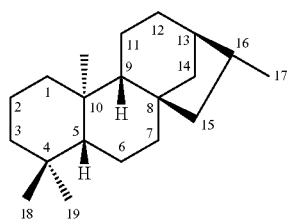

ent-Kaurene or ent-Kaurane or ent-Kaurenoid

Hydrocarbyl

The term "hydrocarbyl" as used herein includes reference to a moiety consisting exclusively of hydrogen and carbon atoms; such a moiety may comprise an aliphatic and/or an aromatic moiety. The moiety may comprise 1, 2, 3, 4, 5, 6, 7, 8, 9, 10, 11, 12, 13, 14, 15, 16, 17, 18, 19 or 20 carbon atoms. Examples of hydrocarbyl groups include $C_{1-6}$ alkyl (e.g. $C_1$, $C_2$, $C_3$ or $C_4$ alkyl, for example methyl, ethyl, propyl, isopropyl, n-butyl, sec-butyl or tert-butyl); $C_{1-6}$ alkyl substituted by aryl (e.g. benzyl) or by cycloalkyl (e.g. cyclopropylmethyl); cycloalkyl (e.g. cyclopropyl, cyclobutyl, cyclopentyl or cyclohexyl); aryl (e.g. phenyl, naphthyl or fluorenyl) and the like.

Alkyl

The terms "alkyl" and "$C_{1-6}$ alkyl" as used herein include reference to a straight or branched chain alkyl moiety having 1, 2, 3, 4, 5 or 6 carbon atoms. This term includes reference to groups such as methyl, ethyl, propyl (n-propyl or isopropyl), butyl (n-butyl, sec-butyl or tert-butyl), pentyl, hexyl and the like. In particular, the alkyl moiety may have 1, 2, 3 or 4 carbon atoms.

Alkenyl

The terms "alkenyl" and "$C_{2-6}$ alkenyl" as used herein include reference to a straight or branched chain alkyl moiety having 2, 3, 4, 5 or 6 carbon atoms and having, in addition, at least one double bond, of either E or Z stereochemistry where applicable. This term includes reference to groups such as ethenyl, 2-propenyl, 1-butenyl, 2-butenyl, 3-butenyl, 1-pentenyl, 2-pentenyl, 3-pentenyl, 1-hexenyl, 2-hexenyl and 3-hexenyl and the like.

Alkynyl

The terms "alkynyl" and "$C_{2-6}$ alkynyl" as used herein include reference to a straight or branched chain alkyl moiety having 2, 3, 4, 5 or 6 carbon atoms and having, in addition, at least one triple bond. This term includes reference to groups such as ethynyl, 1-propynyl, 2-propynyl, 1-butynyl, 2-butynyl, 3-butynyl, 1-pentynyl, 2-pentynyl, 3-pentynyl, 1-hexynyl, 2-hexynyl and 3-hexynyl and the like.

Alkoxy

The terms "alkoxy" and "$C_{1-6}$ alkoxy" as used herein include reference to —O-alkyl, wherein alkyl is straight or branched chain and comprises 1, 2, 3, 4, 5 or 6 carbon atoms. In one class of embodiments, alkoxy has 1, 2, 3 or 4 carbon atoms. This term includes reference to groups such as methoxy, ethoxy, propoxy, isopropoxy, butoxy, tert-butoxy, pentoxy, hexoxy and the like.

Cycloalkyl

The term "cycloalkyl" as used herein includes reference to an alicyclic moiety having 3, 4, 5, 6, 7 or 8 carbon atoms. The group may be a bridged or polycyclic ring system. More often cycloalkyl groups are monocyclic. This term includes reference to groups such as cyclopropyl, cyclobutyl, cyclopentyl, cyclohexyl, norbornyl, bicyclo[2.2.2]octyl and the like.

Aryl

The term "aryl" as used herein includes reference to an aromatic ring system comprising 6, 7, 8, 9, 10, 11, 12, 13, 14, 15 or 16 ring carbon atoms. Aryl is often phenyl but may be a polycyclic ring system, having two or more rings, at least one of which is aromatic. This term includes reference to groups such as phenyl, naphthyl, fluorenyl, azulenyl, indenyl, anthryl and the like.

Cyclic Group

"Cyclic group" means a ring or ring system, which may be unsaturated or partially unsaturated but is usually saturated, typically containing 5 to 13 ring-forming atoms, for example a 5- or 6-membered ring. The ring or ring system may be substituted with one or more hydrocarbyl groups. Cyclic group includes carbocyclyl and heterocyclyl moieties.

Carbocyclyl

The term "carbocyclyl" as used herein includes reference to a saturated (e.g. cycloalkyl) or unsaturated (e.g. aryl) ring moiety having 3, 4, 5, 6, 7, 8, 9, 10, 11, 12, 13, 14, 15 or 16 carbon ring atoms. In particular, carbocyclyl includes a 3- to 10-membered ring or ring system and, in particular, 5- or 6-membered rings, which may be saturated or unsaturated. The ring or ring system may be substituted with one or more hydrocarbyl groups. A carbocyclic moiety is, for example, selected from cyclopropyl, cyclobutyl, cyclopentyl, cyclohexyl, norbornyl, bicyclo[2.2.2]octyl, phenyl, naphthyl, fluorenyl, azulenyl, indenyl, anthryl and the like.

Heterocyclyl

The term "heterocyclyl" as used herein includes reference to a saturated (e.g. heterocycloalkyl) or unsaturated (e.g. heteroaryl) heterocyclic ring moiety having from 3, 4, 5, 6, 7, 8, 9, 10, 11, 12, 13, 14, 15 or 16 ring atoms, at least one of which is selected from nitrogen, oxygen, phosphorus, silicon and sulphur. In particular, heterocyclyl includes a 3- to 10-membered ring or ring system and more particularly a 5- or 6-membered ring, which may be saturated or unsaturated. The ring or ring system may be substituted with one or more hydrocarbyl groups.

A heterocyclic moiety is, for example, selected from oxiranyl, azirinyl, 1, 2-oxathiolanyl, imidazolyl, thienyl, furyl, tetrahydrofuryl, pyranyl, thiopyranyl, thianthrenyl, isobenzofuranyl, benzofuranyl, chromenyl, 2H-pyrrolyl, pyrrolyl, pyrrolinyl, pyrrolidinyl, pyrrolizidinyl, imidazolyl, imidazolidinyl, benzimidazolyl, pyrazolyl, pyrazinyl, pyrazolidinyl, thiazolyl, isothiazolyl, dithiazolyl, oxazolyl, isoxazolyl, pyridyl, pyrazinyl, pyrimidinyl, piperidyl, piperazinyl, pyridazinyl, morpholinyl, thiomorpholinyl, especially thiomorpholino, indolizinyl, isoindolyl, 3H-indolyl, indolyl, benzimidazolyl, cumaryl, indazolyl, triazolyl, tetrazolyl, purinyl, 4/V-quinolizinyl, isoquinolyl, quinolyl, tetrahydroquinolyl, tetrahydroisoquinolyl, decahydroquinolyl, octahydroisoquinolyl, benzofuranyl, dibenzofuranyl, benzothiophenyl, dibenzothiophenyl, phthalazinyl, naphthyridinyl, quinoxalyl, quinazolinyl, quinazolinyl, cinnolinyl, pteridinyl, carbazoiyl, β-carbolinyl, phenanthridinyl, acridinyl, perimidinyl, phenanthrolinyl, furazanyl, phenazinyl, phenothiazinyl, phenoxazinyl, chromenyl, isochromanyl, chromanyl and the like.

Heterocycloalkyl

The term "heterocycloalkyl" as used herein includes reference to a saturated heterocyclic moiety having 3, 4, 5, 6 or 7 ring carbon atoms and 1, 2, 3, 4 or 5 ring heteroatoms selected from nitrogen, oxygen, phosphorus and sulphur. The group may be a polycyclic ring system but more often is monocyclic. This term includes reference to groups such as azetidinyl, pyrrolidinyl, tetrahydrofuranyl, piperidinyl, oxiranyl, pyrazolidinyl, imidazolyl, indolizidinyl, piperazinyl, thiazolidinyl, morpholinyl, thiomorpholinyl, quinolizidinyl and the like. The ring or ring system may be substituted with one or more hydrocarbyl groups.

Heteroaryl

The term "heteroaryl" as used herein includes reference to an aromatic heterocyclic ring system having 5, 6, 7, 8, 9, 10, 11, 12, 13, 14, 15 or 16 ring atoms, at least one of which is selected from nitrogen, oxygen and sulphur. The group may be a polycyclic ring system, having two or more rings, at least one of which is aromatic, but is more often monocyclic. The ring or ring system may be substituted with one or more hydrocarbyl groups. This term includes reference to groups such as pyrimidinyl, furanyl, benzo[b]thiophenyl, thiophenyl, pyrrolyl, imidazolyl, pyrrolidinyl, pyridinyl, benzo[b]furanyl, pyrazinyl, purinyl, indolyl, benzimidazolyl, quinolinyl, phenothiazinyl, triazinyl, phthalazinyl, 2H-chromenyl, oxazolyl, isoxazolyl, thiazolyl, isoindolyl, indazolyl, purinyl, isoquinolinyl, quinazolinyl, pteridinyl and the like.

Halogen

The term "halogen" as used herein includes reference to F, Cl, Br or I.

Halogen Containing Moiety

The expression "halogen containing moiety" as used herein includes reference to a moiety comprising 1 to 30 plural valence atoms selected from carbon, nitrogen, oxygen and sulphur which moiety includes at least one halogen. The moiety may be hydrocarbyl for example $C_{1-6}$ alkyl or $C_{1-6}$ alkoxy, or carbocyclyl for example aryl.

Substituted

The term "substituted" as used herein in reference to a moiety means that one or more, especially up to 5, more especially 1, 2 or 3, of the hydrogen atoms in said moiety are replaced independently of each other by the corresponding number of the described substituents. The term "optionally substituted" as used herein means substituted or un-substituted. It will, of course, be understood that substituents are only at positions where they are chemically possible, the person skilled in the art being able to decide (either experimentally or theoretically) without inappropriate effort whether a particular substitution is possible.

Enantiomer

The term "enantiomer" as used herein means one of two stereoisomers that have mirror images of one another.

Racemate

The term "racemate" as used herein means a mixture of equal amounts of enantiomers of a chiral molecule.

Diastereomer

The term "diastereomer" as used herein means one of a class of stereoisomers that are not enantiomers, but that have different configurations at one or more of the equivalent chiral centers. Example of diasteromers are epimers that differ in configuration of only one chiral center.

Stereoisomer

The term "stereoisomer" as used herein means one of a class of isomeric molecules that have the same molecular formula and sequence of bonded atoms, but different three-dimensional orientations of their atoms in space.

Prodrug

A prodrug is a medication that is administered as an inactive (or less than fully active) chemical derivative that is subsequently converted to an active pharmacological agent in the body, often through normal metabolic processes.

Independently

Where two or more moieties are described as being "each independently" selected from a list of atoms or groups, this means that the moieties may be the same or different. The identity of each moiety is therefore independent of the identities of the one or more other moieties.

Embodiments of the present invention are described below. Preferred features of each aspect of the present invention are as for each of the other aspects mutatis mutandis. Moreover, it will be appreciated that the features specified in each embodiment may be combined with other specified features, to provide further embodiments.

Compounds of the Present Invention

The present invention relates to a group of derivatives synthesized based on the ent-kaurane diterpenoid flexicaulin A and the methods to synthesize such diterpenoid derivatives. The invention also relates to the chemical entities of such synthetic diterpene compounds in the manufacture of a medicament for the treatment of tumors or cancers.

In an exemplary embodiment, the present invention provides a compound of formula (IV):

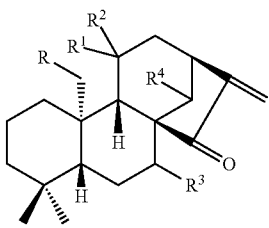

(IV)

wherein $R^1$ and $R^2$ are taken together with the carbon atoms to which they are attached to form a carboxyl groups (C=O); or while one of $R^1$ and $R^2$ is hydroxyl group, $R^3$ and $R^4$ are taken together with the carbon atoms to which they are attached to form a heterocyclyl group, and R and the other one of $R^1$ and $R^2$ are taken together with the carbon atoms to which they are attached to form a heterocyclyl group; while R is selected from —$OR^5$ and —$OC(O)R^5$, $R^3$ and $R^4$ are taken together with the carbon atoms to which they are attached to form a heterocyclyl group optionally substituted with 1, 2, 3, 4 or 5 $R^6$; or while R is selected from —$OR^7$ and —$C(O)R^7$, $R^1$ and $R^2$ are taken together with the carbon atoms to which they are attached to form a carboxyl groups (C=O), and $R^3$ and $R^4$ are both hydroxyl groups; $R^5$ is independently hydrogen or selected from hydrocarbyl and heterocyclyl, either of which is optionally substituted with 1, 2, 3, 4 or 5 $R^8$; $R^6$ is independently selected from hydrogen, halogen, trifluoromethyl, cyano, nitro, hydrocarbyl optionally substituted with 1, 2, 3, 4 or 5 $R^8$, heterocyclyl optionally substituted with 1, 2, 3, 4 or 5 $R^8$, —$OR^9$, —$C(O)R^{10}$, —$C(O)N(R^9)R^{10}$, —$C(O)OR^9$, —$OC(O)R^9$, —$S(O)_2R^9$, —$S(O)_2N(R^9)R^{10}$, and —$N(R^9)R^{10}$; $R^7$ is selected from hydrocarbyl and heterocyclyl, either of which is optionally substituted with 1, 2, 3, 4 or 5 $R^8$; $R^8$ is independently selected from halogen, trifluoromethyl, cyano, nitro, oxo, —$OR^9$, —$C(O)R^{10}$, —$C(O)N(R^9)R^{10}$, —$C(O)OR^9$, —$OC(O)R^{10}$, —$S(O)_2R^9$, —$S(O)_2N(R^9)R^{10}$, and —$N(R^9)R^{10}$; $R^9$ and $R^{10}$ are each independently hydrogen or selected from hydrocarbyl and heterocyclyl, either of which is optionally substituted with 1, 2, 3, 4 or 5 substituents independently selected from halogen, cyano, amino, hydroxy, $C_{1-6}$ alkyl and $C_{1-6}$ alkoxy; or an enantiomer thereof; or a pharmaceutically acceptable salt or prodrug thereof.

In other embodiment, the present invention provides compounds of formula (I), (II) or (III):

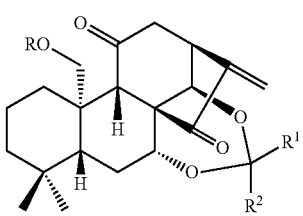

(I)

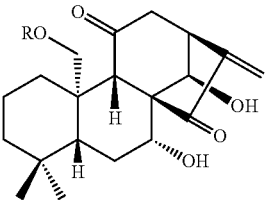

(II)

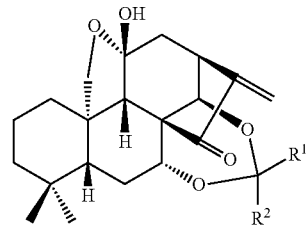

(III)

wherein $R^1$ and $R^2$ are each independently selected from hydrogen, halogen, alkoxy, hydrocarbyl optionally substituted with 1, 2, 3, 4 or 5 $R^3$, or heterocyclyl optionally substituted with 1, 2, 3, 4 or 5 $R^3$; $R^3$ is independently selected from hydrogen, halogen, trifluoromethyl, cyano, nitro, hydrocarbyl optionally substituted with 1, 2, 3, 4 or 5 $R^4$, heterocyclyl optionally substituted with 1, 2, 3, 4 or 5 $R^4$, —$OR^5$, —$C(O)R^6$, —$C(O)N(R^5)R^6$, —$C(O)OR^5$, —$OC(O)R^5$, —$S(O)_2R^5$, —$S(O)_2N(R^5)R^6$, and —$N(R^5)R^6$; $R^4$ is independently selected from halogen, trifluoromethyl, cyano, nitro, oxo, —$OR^5$, —$C(O)R^6$, —$C(O)N(R^5)R^6$, —$C(O)OR^5$, —$OC(O)R^6$, —$S(O)_2R^5$, —$S(O)_2N(R^5)R^6$, —$N(R^5)R^6$; $R^5$ and $R^6$ are each independently hydrogen or selected from hydrocarbyl and heterocyclyl, either of which is optionally substituted with 1, 2, 3, 4 or 5 substituents independently selected from halogen, cyano, amino, hydroxy, $C_{1-6}$ alkyl and $C_{1-6}$ alkoxy; R is selected from $R^7$ and (C=O)$R^7$; $R^7$ according to formula (I) is independently selected from hydrogen and hydrocarbyl optionally substituted with 1, 2, 3, 4 or 5 substituents independently selected from halogen, cyano, amino, hydroxy, $C_{1-6}$ alkyl and $C_{1-6}$ alkoxy, while $R^7$ according to formula (II) is hydrocarbyl optionally substituted with 1, 2, 3, 4 or 5 substituents independently selected from halogen, cyano, amino, hydroxy, $C_{1-6}$ alkyl and $C_{1-6}$ alkoxy, meaning that R is not hydrogen atom in formula (II); or an enantiomer thereof; or a pharmaceutically acceptable salt or prodrug thereof.

Examples of the compounds of the present invention include those shown below. It will of course be appreciated that, where appropriate, each compound may be in the form of the free compound, an enantiomer, an acid or base addition salt, or a prodrug.

EXAMPLES

According to previous studies, ent-kaurane diterpenoids, flexicaulin A (FA) and pseudoirroratin A (PA) (FIG. 1) have been demonstrated to exert remarkable anti-proliferative actions against diverse tumor/cancer cell lines with low $IC_{50}$ values. The anti-proliferative effect of PA is more potent than FA; however, PA can merely be isolated from very scanty sources. To this end, we discover a facile semi-synthetic approach for generating PA from FA. During the semi-synthesis pathway, the FA derivatives (i.e. FA1-FA4) are generated as intermediate products (Scheme 1 and Scheme 2).

Scheme 1.
Chemical synthesis of FA1, FA2, FA3 and PA from FA.

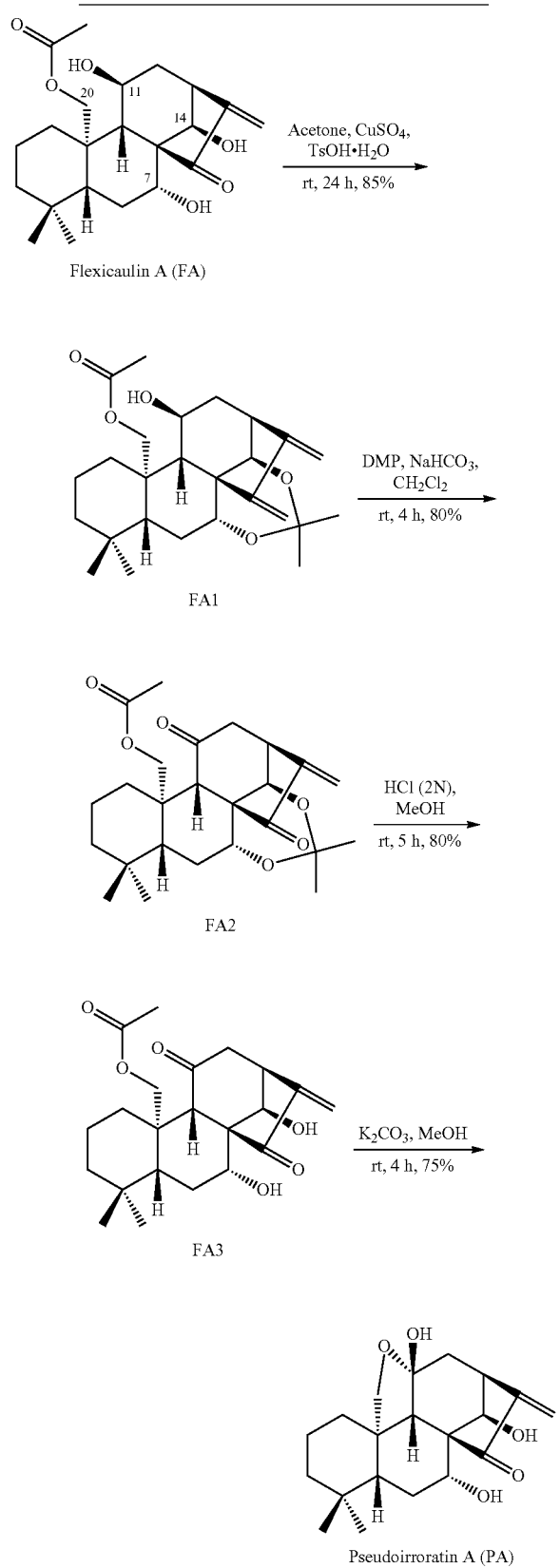

Scheme 2. Chemical synthesis of FA4 from FA2.

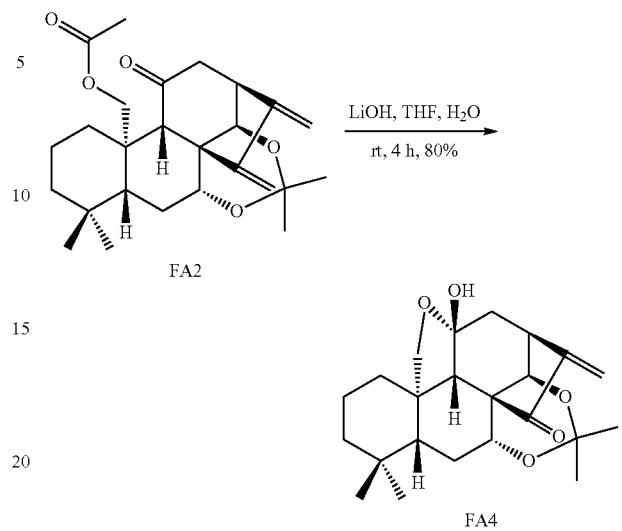

The inventors thus examine the anti-proliferative effect of the highly similar compounds FA, FA1, FA2, FA3, FA4 and PA in four common human carcinoma cell lines, HCT-116, A375, HT-29 and PANC-1. From the sulforhodamine B assay result, the anti-proliferative effect of FA3 is much more potent than its synthesizing scaffold FA and is very comparable to its end-product PA (Table 1). FA3 is found the most potent among all FA intermediates.

TABLE 1

Anti-proliferative activities of FA, FA derivatives and PA in various human carcinoma cell lines. HCT-116 and HT-29 are human colorectal carcinoma cell lines; A375 is a human melanoma cell line and PANC-1 is a human pancreatic ductal adenocarcinoma cell line.

| Compound | HCT-116 | A375 | HT-29 | PANC-1 |
|---|---|---|---|---|
| FA | 721.5 | 1624 | 973.2 | 1024 |
| FA1 | 1373 | 1975 | >2000 | >2000 |
| FA2 | >2000 | >2000 | >2000 | >2000 |
| FA3 | 273.9 | 668.5 | 424.4 | 413.4 |
| FA4 | 980.4 | >2000 | >2000 | >2000 |
| PA | 270.2 | 873.7 | 419.4 | 439.6 |

Results are expressed as $IC_{50}$ values (concentration required to inhibit cell growth by 50%) in ng/mL, and data are obtained from six individual experiments (n=8 per experiment).

Figure 2:
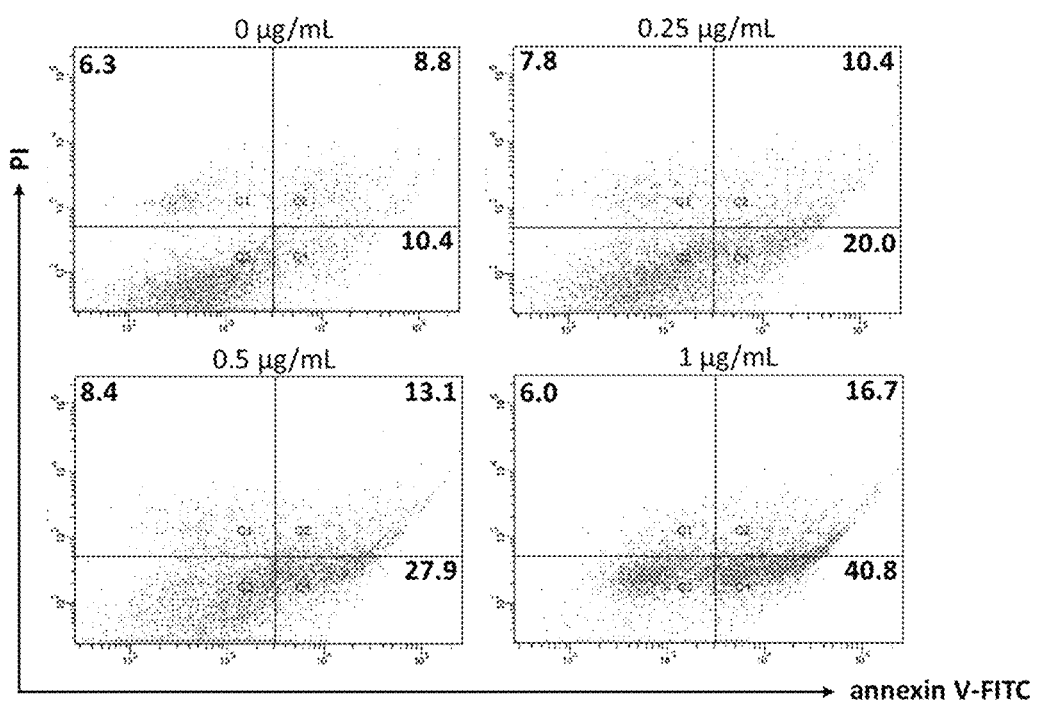
FIG. 2 shows the induction of apoptotic events in HCT-116 cells by incubation with FA3 at 0, 0.25, 0.5 and 1.0 μg/mL for 48 hours. From the flow cytometric analysis, the staining percentage of annexin V/FITC and propidium iodide (PI) is detected as percentage at Q1: necrosis (upper left quarter); Q2: late apoptosis (upper right quarter); Q3: live (lower left quarter); Q4: early apoptosis (lower right quarter).
Figure 3:
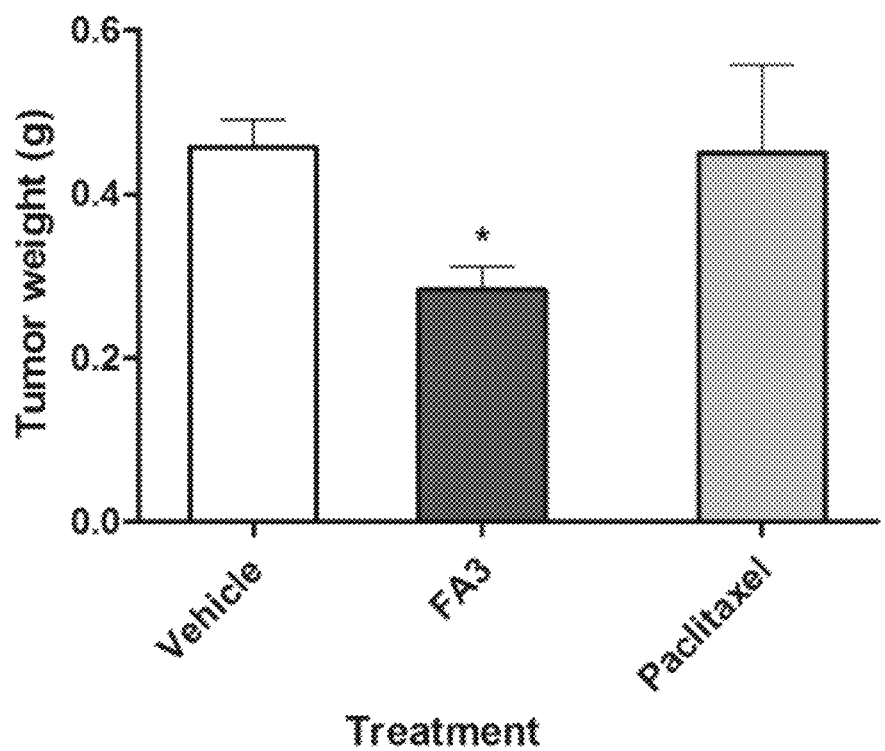
FIG. 3 shows the reduction of tumor growth in terms of tumor weight (g) in HCT-116 colon carcinoma cell-bearing nude mice after administering vehicle or FA3 or paclitaxel treatment at day 21 (* $p<0.05$ when comparing to the vehicle treatment group).
Figure 4:
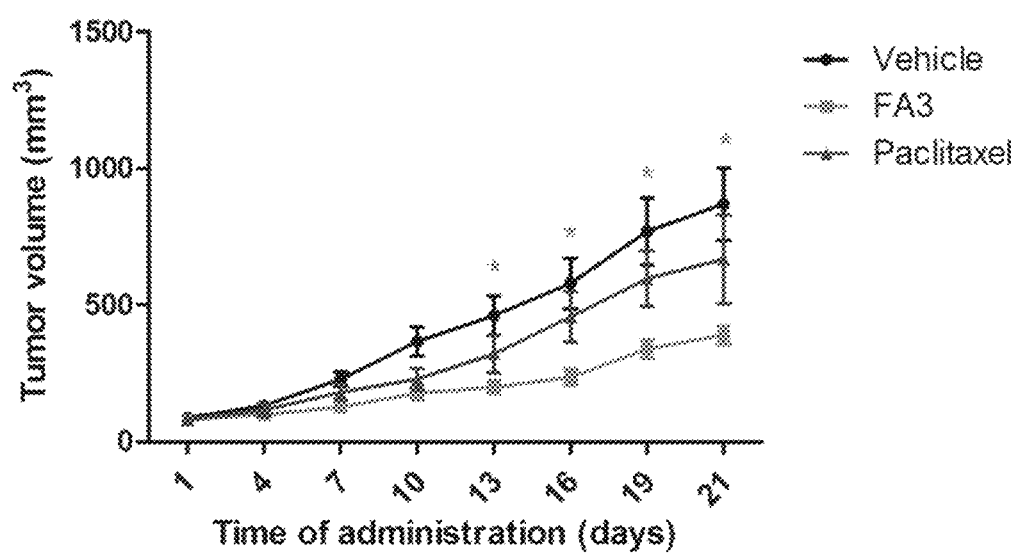
FIG. 4 shows the reduction of tumor growth in terms of tumor volume ($mm^3$) in HCT-116 colon carcinoma cell-bearing nude mice after administering vehicle or FA3 or paclitaxel treatment for 21 days (* p<0.05 when comparing to the vehicle treatment group).
Figure 5:
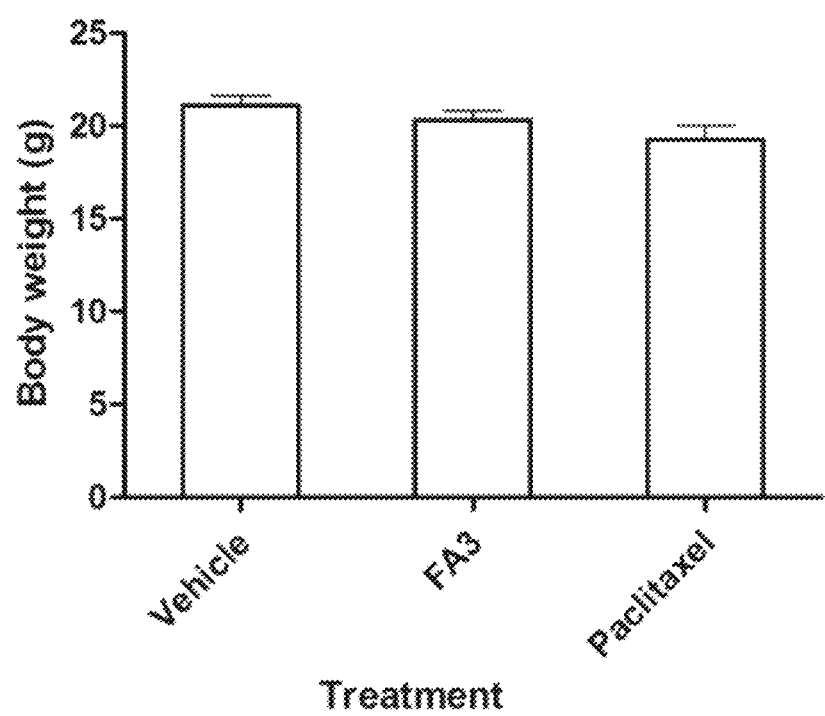
FIG. 5 shows the change of body weight of the HCT-116 colon carcinoma cell-bearing nude mice after administering vehicle solution or FA3 (10 mg/kg) or paclitaxel (10 mg/kg) treatment for 21 days.
Figure 6:
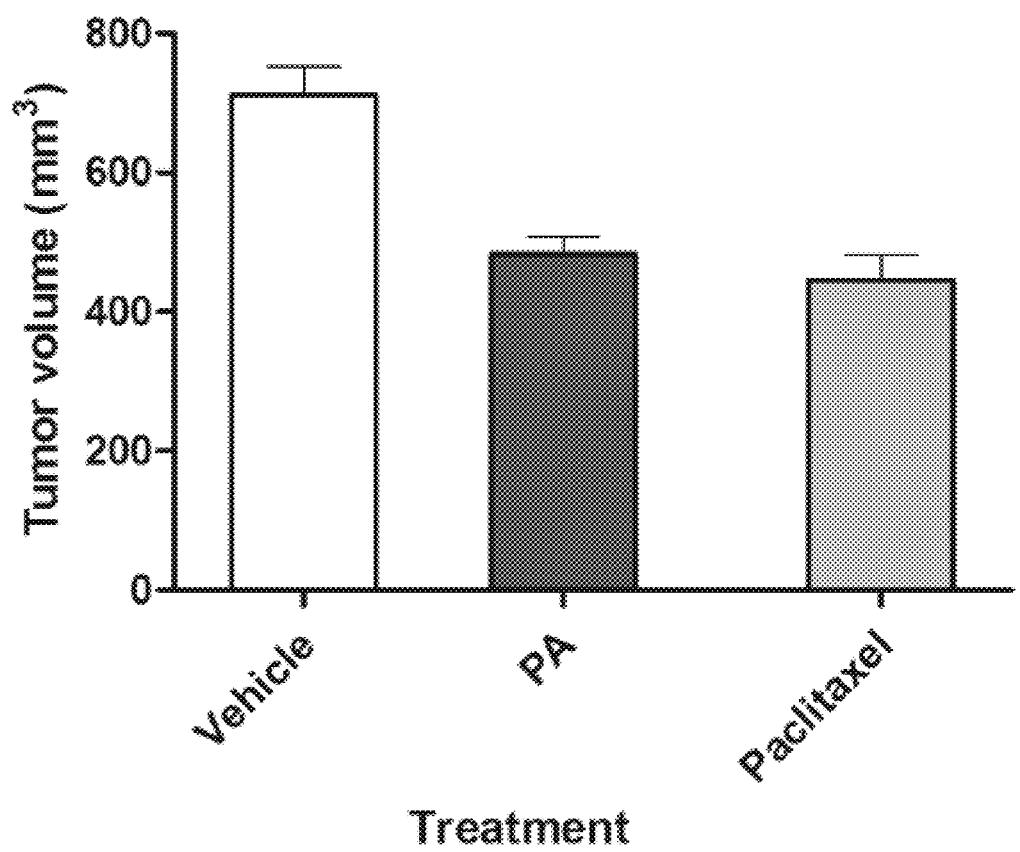
FIG. 6 shows the reduction of tumor growth in terms of tumor volume (mm³) in HCT-116 colon carcinoma cell-bearing nude mice after administering vehicle or PA or paclitaxel treatment at day 21.

Substantial increase in the degree of apoptosis is obtained from the FA3-treated carcinoma cells in a concentration-dependent fashion (FIG. 2). Importantly, the growth of xenograft tumor, in terms of weight (FIG. 3) and volume (FIG. 4), is more sufficiently restrained by the administration of FA3 when comparing to the mainstay anticancer drug paclitaxel. Importantly, the 21-day administration of FA3 does not lead to a significant loss of body weight (FIG. 5). Such result implies that FA3 is not a toxic substance that causes severe undesirable effects in animals. On the other hand, the antitumor effect of PA is not as efficient as paclitaxel on tumor reduction in xenograft mice (FIG. 6) though it provides a strong anti-proliferative effect against carcinoma cells in vitro.

In conclusion, though the starting scaffold (FA), the end product (PA) and the intermediates (FA1-FA4) share a high similarity structure-wise, they possess diverging potencies against tumor/cancer cell proliferation or tumor growth.

Experiments

The synthesis of FA1: a solution of flexicaulin A (FA, 110 mg, 0.28 mmol) in anhydrous acetone (12 mL) was added anhydrous $CuSO_4$ (447 mg, 2.8 mmol) and catalyzed $TsOH.H_2O$ (5 mg). After being stirring for 24 hours at room temperature under $N_2$ protection, the reaction mixture was alkalified with $Et_3N$ (0.5 ml) and filtered through Celite to afford clear solution. Ethyl acetate was used to wash Celite cake and combined together with the previous organic phase before being dried with anhydrous $Na_2SO_4$. After solvent evaporated, the residue was purified by silica gel chromatography using petroleum ether and ethyl acetate 1:1 as eluent to afford 109 mg white solid of FA1 in 90% yield. $[\alpha]_D^{17}$=-89.9 (c 1.80, MeOH). $^1$H NMR (400 MHz, $CDCl_3$, $\delta$) 6.10 (s, 1 H), 5.42 (s, 1 H), 4.77 (d, J=12.3 Hz, 1 H), 4.41 (d, J=1.4 Hz, 1 H), 4.32 (dd, J=12.5, 6.1 Hz, 1 H), 4.26 (d, J=4.16 Hz, 1 H), 4.16 (d, J=12.5 Hz, 1H), 3.02 (s, 1 H), 2.34 (ddd, J=14.6, 4.8, 2.8 Hz, 1 H), 2.15-2.00 (m, 6 H), 1.81 (q, J=12.9 Hz, 1 H), 1.56 (s, 1 H), 1.54 (s, 3 H), 1.52-1.45 (m, 3 H), 1.25-1.23 (m, 4 H), 1.07 (dd, 12.9, 1.9 Hz, 1 H), 0.94 (s, 3 H), 0.91 (s, 3 H), 0.88-0.87 (m, 1 H). $^{13}$C NMR (100 MHz, $CDCl_3$, $\delta$) 205.5, 170.7, 147.4, 116.1, 97.4, 71.7, 70.7, 65.3, 64.0, 63.5, 52.7, 52.0, 42.0, 41.3, 40.7, 38.1, 33.9, 33.6, 30.7, 27.2, 25.4, 22.5, 21.2, 18.1. HRMS (MALDI-TOF) m/z for $C_{25}H_{36}O_6Na$ 455.2415; found, 455.2435 $[M+Na]^+$.

For the synthesis of FA2, a solution of FA1 (84.5 mg, 0.2 mmol) in $CH_2Cl_2$ (20 mL) was added $DMP.3AcOH$ (254 mg, 0.6 mmol) and $NaHCO_3$ (168 mg, 2.0 mmol) in an ice-water bath. After being stirring overnight at room temperature under $N_2$ protection, the reaction mixture was filtered through Celite, washed with $CH_2Cl_2$ and dried with anhydrous $Na_2SO_4$. After solvent removed, the residue was purified by silica gel chromatography using petroleum ether and ethyl acetate 3:1 as eluent to afford 73 mg white solid of FA2 in 85% yield. $[\alpha]_D^{19}$=-20.6 (c 1.25, MeOH). $^1$H NMR (400 MHz, $CDCl_3$, $\delta$) 6.24 (s, 1 H), 5.55 (s, 1 H), 4.98 (d, J=12.2 Hz, 1 H), 4.77 (d, J=1.2 Hz, 1 H), 4.36 (q, J=6.2 Hz, 1 H), 4.13 (d, J=12.1 Hz, 1 H), 3.23 (s, 1 H), 3.07 (dd, J=16.4, 3.8 Hz, 1 H), 2.57 (dq, J=16.4, 1.6 Hz, 1 H), 2.14 (ddd, J=13.4, 6.2, 2.1 Hz, 1 H), 2.01 (s, 3 H), 1.98-1.94 (m, 1 H), 1.86 (q, J=12.8 Hz, 1 H), 1.61 (d, J=6.2 Hz, 1 H), 1.60 (s, 3 H), 1.50-1.40 (m, 3 H), 1.28 (s, 3 H), 1.25-1.18 (m, 1 H), 1.07-1.00 (m, 2 H), 0.94 (s, 3 H), 0.92 (s, 3 H). $^{13}$C NMR (100 MHz, $CDCl_3$, $\delta$) 205.2, 203.4, 170.1, 145.1, 121.2, 97.8, 70.7, 69.8, 64.0, 62.7, 52.9, 51.4, 48.0, 44.1, 42.4, 41.2, 34.3, 33.4(d), 30.2, 27.1, 25.4, 22.7, 20.8, 17.9. HRMS (MALDI-TOF) m/z for $C_{25}H_{34}O_6Na$ 453.2259; found, 453.2275 $[M+Na]^+$.

For the synthesis of FA3, a solution of FA2 (90 mg, 0.21 mmol) in MeOH (25 mL) was added dropwise 2N HCl (1 ml, Con. HCl diluted in MeOH) and $H_2O$ (0.5 ml) at room temperature and stirred overnight. After solvent evaporated, the residue was purified by silica gel chromatography using petroleum ether and ethyl acetate 1:1 as eluent to afford 68 mg white solid of FA3 in 84% yield. $[\alpha]_D^{18}$=-36.2 (c 1.00, MeOH). $^1$H NMR (400 MHz, $CDCl_3$, $\delta$) 6.24 (s, 1 H), 5.92 (br, 1 H), 5.57 (s, 1 H), 5.14, (s, 1 H), 5.04 (d, J=12.5 Hz, 1 H), 4.48 (q, J=12.3 Hz, 1 H), 4.17 (d, J=12.4 Hz, 1 H), 3.54 (br, 1 H), 3.24-3.19 (m, 2 H), 2.47 (dt, J=15.8, 1.4 Hz, 1 H), 2.04 (dd, J=13.2, 3.1 Hz, 1 H), 2.01 (s, 3 H), 1.86-1.77 (m, 3 H), 1.51-1.42 (m, 3 H), 1.24-1.13 (m, 3 H), 0.97 (s, 3 H), 0.94 (m, 3 H). $^{13}$C NMR (100 MHz, $CDCl_3$, $\delta$) 205.7, 205.1, 170.1, 146.1, 122.1, 75.3, 73.9, 65.2, 62.3, 59.5, 53.0, 47.8, 44.8, 44.7, 40.9, 34.4, 34.0, 33.4, 27.9, 22.7, 20.8, 18.0. HRMS (MALDI-TOF) m/z for $C_{22}H_{30}O_6Na$ 413.1946; found, 413.1932 $[M+Na]^+$.

For the synthesis of PA, a solution of FA3 (15 mg, 0.038 mmol) in THF (16 mL) was added dropwise an aqueous solution of LiOH (1 ml, 0.12 M) at a room temperature. After being stirring overnight under $N_2$ protection, the reaction solution changed in yellow, then was quenched with water and extracted with ethyl acetate. The combined organic phase was dried over with $Na_2SO_4$ and evaporated in vacuum, meanwhile the residue was purified by silica gel chromatography using petroleum ether and ethyl acetate 1:1 as eluent to afford 6 mg white solid of PA in 45% yield. $[\alpha]_D^{17}$=-158.5 (c 0.50, MeOH).

PA: $^1$H NMR (400 MHz, Py-$d_5$, $\delta$) 6.22 (s, 1 H), 5.42 (s, 1 H), 5.38 (s, 1 H), 4.96 (brd, 3 H) 4.84 (dt, J=11.2, 3.6 Hz, 1 H), 4.16 (d, J=8.6 Hz, 1 H), 4.06 (d, J=8.2 Hz, 1 H), 3.38 (d, J=13.3 Hz, 1 H), 3.27 (d, J=9.2 Hz, 1 H), 3.22 (dd, J=13.7, 9.0 Hz, 1 H), 2.28 (s, 1 H), 2.18 (d, J=13.8 Hz, 1 H), 2.13 (d, J=2.4 Hz, 1 H), 1.96 (q, J=12.4 Hz, 1 H), 1.59-1.53 (m, 1 H), 1.49 (dd, J=12.7, 1.9 Hz, 1 H), 1.37 (m, 1 H), 1.24 (d, J=12.8 Hz, 1 H), 1.14-1.06 (m, 2 H), 0.82 (s, 3 H), 0.64 (s, 3 H). $^{13}$C NMR (100 MHz, Py-$d_5$, $\delta$) 208.7, 153.2, 116.3, 103.5, 74.8, 74.0, 69.2, 62.6, 57.8, 51.1, 50.3, 46.3, 44.8, 41.4, 39.2, 34.1, 32.3, 28.7, 21.4, 20.1. HRMS (MALDI-TOF) m/z for $C_{20}H_{28}O_5Na$ 371.1829; found, 371.1836 $[M+Na]^+$.

Human colorectal carcinoma HCT-116 and HT-29 cells are routinely maintained in McCoy's 5A medium (Gibco) whereas human melanoma A375 cells and human pancreatic adenocarcinoma PANC-1 cells are cultured in DMEM (Gibco) supplemented with 10% fetal bovine serum (Gibco), 1% penicillin-streptomycin (Gibco) in a 5% CO2, 95% air humidified atmosphere at 37° C.

For the sulforhodamine B assay, different carcinoma cells were seeded in 96-well plates at a density of $5\times10^3$ cells/well and incubated with serial dilutions of ent-kaurene diterpenoids FA, FA1, FA2, FA3, FA4 or PA for 48 hours. After incubation, cells were treated with 50% trichloroacetic acid at 4° C. for at least 30 minutes for protein fixing. Cells were then washed with water 4 times prior to a complete dry down of the culture plate. To each well, 100 μL of 0.4% sulforhodamine B in 1% acetic acid was added. After 30-minute incubation at room temperature, cells were washed with 1% acetic acid 4 times. Fixed proteins were fully solubilized with 10 mM Tris base solution (pH 10, 200 μL/well). Spectrophotometric absorbance of samples were measured at 515 nm using a microplate reader (Bio-rad).

For the flow cytometric assay, HCT-116 cells were seeded in 6-well plates at a density of $1\times10^5$ cells/well and incubated with serial dilutions of FA3 for 48 hours. Cells were collected by centrifugation, re-suspended in 500 μL of binding buffer containing 5 μL of propidium iodide and 5 μL of annexin V-FITC, and incubated for 15 minutes in dark. Signals of the cell suspension were then analyzed using a flow cytometer (BD) for apoptotic events.

For the xenograft experiment, HCT-116 cells were implanted subcutaneously in the right and left flanks ($1\times10^6$ cells in 100 μL) of male BALB/c nude mice (n=10/group), which were SPF class and aged 6-7 weeks old weighing between 20 g-25 g. Tumor size was monitored by measuring two perpendicular diameters with a caliper every other day. When tumors were formed to approximately 100 $mm^3$ seven days after the injection of HCT-116 cells, FA3 or PA was administered (20 mg/kg, every other day by intraperitoneal injection for a total of 21 days). To the paclitaxel group, injection of paclitaxel was given at 10 mg/kg to the nude mice whilst the vehicle group merely received the 2.5% EtOH and Cremphor EL solution, which was the dissolving solution for FA3, PA and paclitaxel. Tumor volume and body weight of mice were recorded at indicated time points during the course of experiment. Tumor volume was calculated as volume=length×width$^2$×0.5. Weight of tumor xenograft was assessed at the time of sacrificed.

Human equivalent dosage is converted from the mouse dosage using the following equation: $D_{human}=D_{mouse} \times k$ (k=0.081) (Regan-Shaw et al. (2007). Disclosure thereof is incorporated herein by its entirety.) Therefore, the human equivalent dosage is 1.62 mg/kg every other day.

The data are presented as mean±standard error of the mean (S.E.M.). Statistical differences among the experimental groups were tested by one-way analysis of variance (ANOVA). P-value<0.05 was considered as statistically significant.

Having now fully described the present invention in some detail by way of illustration and examples for purposes of clarity of understanding, it will be obvious to one of ordinary skill in the art that the same can be performed by modifying or changing the present invention within a wide and equivalent range of conditions, formulations and other parameters without affecting the scope of the present invention or any specific embodiment thereof, and that such modifications or changes are intended to be encompassed within the scope of the appended claims. The terms and expressions which have been employed are used as terms of description and not of limitation, and there is no intention that in the use of such terms and expressions of excluding any equivalents of the features shown and described or portions thereof, but it is recognized that various modifications are possible within the scope of the present invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of the present invention.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. In each instance herein any of the terms "comprising", "consisting essentially of" and "consisting of" may be replaced with either of the other two terms.

When a group of materials, compositions, components or compounds is disclosed herein, it is understood that all individual members of those groups and all subgroups thereof are disclosed separately. When a Markush group or other grouping is used herein, all individual members of the group and all combinations and subcombinations possible of the group are intended to be individually included in the disclosure. Every formulation or combination of components described or exemplified herein can be used to practice the present invention, unless otherwise stated. Whenever a range is given in the specification, for example, a temperature range, a time range, or a composition range, all intermediate ranges and subranges, as well as all individual values included in the ranges given are intended to be included in the disclosure. In the disclosure and the claims, "and/or" means additionally or alternatively. Moreover, any use of a term in the singular also encompasses plural forms.

All references cited herein are hereby incorporated by reference in their entirety to the extent that there is no inconsistency with the disclosure of this specification. Some references provided herein are incorporated by reference to provide details concerning sources of starting materials, additional starting materials, additional reagents, additional methods of synthesis, additional methods of analysis, additional biological materials, additional cells, and additional uses of the present invention. All headings used herein are for convenience only. All patents and publications mentioned in the specification are indicative of the levels of skill of those skilled in the art to which the present invention pertains, and are herein incorporated by reference to the same extent as if each individual publication, patent or patent application was specifically and individually indicated to be incorporated by reference. References cited herein are incorporated by reference herein in their entirety to indicate the state of the art as of their publication or filing date and it is intended that this information can be employed herein, if needed, to exclude specific embodiments that are in the prior art. For example, when composition of matter are claimed, it should be understood that compounds known and available in the art prior to Applicant's invention, including compounds for which an enabling disclosure is provided in the references cited herein, are not intended to be included in the composition of matter claims herein.

If desired, the different functions discussed herein may be performed in a different order and/or concurrently with each other. Furthermore, if desired, one or more of the above-described functions may be optional or may be combined.

While the foregoing invention has been described with respect to various embodiments and examples, it is understood that other embodiments are within the scope of the present invention as expressed in the following claims and their equivalents. Moreover, the above specific examples are to be construed as merely illustrative, and not limitative of the reminder of the disclosure in any way whatsoever. Without further elaboration, it is believed that one skilled in the art can, based on the description herein, utilize the present invention to its fullest extent. All publications recited herein are hereby incorporated by reference in their entirety.

INDUSTRIAL APPLICABILITY

The present invention relates to a group of derivatives synthesized based on the ent-kaurane diterpenoid flexicaulin A and the methods to synthesize such diterpenoid derivatives. In particular, the chemical entities of such synthetic diterpene compounds in the manufacture of a medicament is for the treatment of tumors or cancers.

What is claimed is:
1. A compound of formula (IV):

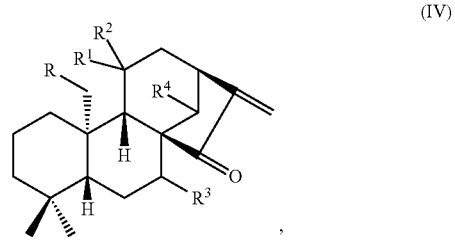

wherein $R^1$ and $R^2$ are taken together with the carbon atoms to which they are attached to form a carboxyl groups (C=O); or while one of $R^1$ and $R^2$ is hydroxyl group, $R^3$ and $R^4$ are taken together with the carbon atoms to which they are attached to form a two oxygen atoms containing 6-member ring heterocyclyl group optionally substituted with two $R^6$, and R and the other one of $R^1$ and $R^2$ are taken together with the carbon atoms to which they are attached to form a one oxygen atom containing a 5-member ring heterocyclyl group;

while R is selected from —$OR^5$ or —$OC(O)R^5$, $R^3$ and $R^4$ are taken together with the carbon atoms to which they are attached to form a 6-member ring heterocyclyl group optionally substituted with two $R^6$, and said 6-member ring heterocyclyl group contains two oxygen atoms; or while R is —$OR^7$ or —$OC(O)R^7$, $R^3$ and $R^4$ are both hydroxyl groups, wherein $R^7$ is $C_{1-6}$ alkyl group;

$R^5$ is hydrogen or $C_{1-6}$ alkyl group $R^6$ is hydrogen or $C_{1-6}$ alkyl group;

or an enantiomer thereof;

or a pharmaceutically acceptable salt thereof.

2. The compound of claim 1, wherein said compound is an optically pure stereoisomer, an enantiomer, a racemate, or a diastereomer.

3. A pharmaceutical composition comprising an effective amount of the compound of claim 1 and a pharmaceutically acceptable carrier thereof.

4. The compound of claim 1, wherein said compound is represented by formula FA2 or FA4:

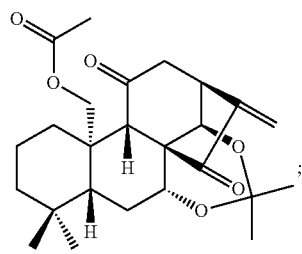

FA2

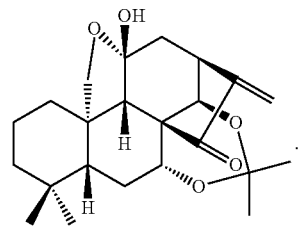

FA4

5. The compound of claim 1, wherein said compound is represented by formula (I), (II) or (III):

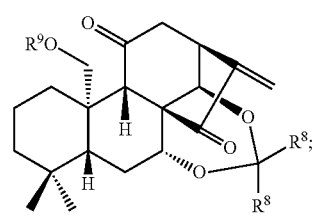

(I)

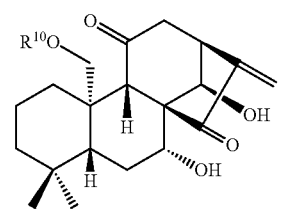

(II)

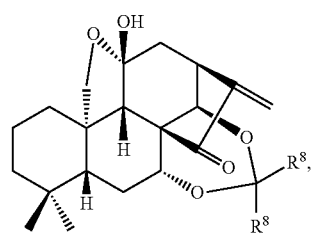

(III)

wherein $R^8$ is hydrogen or $C_{1-6}$ alkyl group;

$R^9$ is $R^{11}$ or (C=O)$R^{11}$;

$R^{10}$ is $R^{12}$ or (C=O)$R^{12}$;

$R^{11}$ is hydrogen or $C_{1-6}$ alkyl;

$R^{12}$ is $C_{1-6}$ alkyl group;

or an enantiomer thereof;

or a pharmaceutically acceptable salt thereof.

6. The compound of claim 5, wherein said compound is an optically pure stereoisomer, an enantiomer, a racemate, or a diastereomer.

7. A pharmaceutical composition comprising an effective amount of the compound of claim 5 and a pharmaceutically acceptable carrier thereof.

8. A method of synthesizing the compound of claim 4 from Flexicaulin A comprising:

adding a solution of Flexicaulin A at about 110 mg or 0.28 mmol into about 12 mL of an anhydrous acetone with anhydrous $CuSO_4$ at about 447 mg or 2.8 mmol and about 5 mg of catalyzed TsOH.$H_2O$ to form a mixture;

stirring the mixture for 24 hours at room temperature under $N_2$ protection;

alkalifying the mixture with about 0.5 mL of $Et_3N$ and filtering through Celite to afford a clear solution;

washing Celite with Ethyl acetate and combining the clear solution with the organic phase previously separated before being dried with anhydrous $Na_2SO_4$;

evaporating residual solvent from said combination of clear solution and organic phase;

purifying residue by silica gel chromatography using petroleum ether and ethyl acetate at 1:1 ratio as an eluent to afford 109 mg white solid of a FA1:

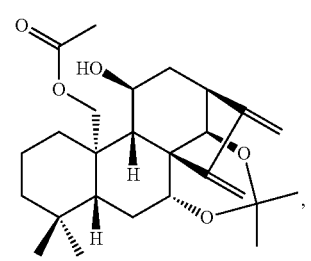

FA1 in 90% yield;

adding a solution of FA1 at about 84.5 mg or 0.2 mmol in about 20 mL of $CH_2Cl_2$ with DMP.3AcOH at about 254 mg or 0.6 mmol and $NaHCO_3$ at about 168 mg or 2.0 mmol in an ice-water bath to form a mixture;

stirring the mixture overnight at room temperature under $N_2$ protection;

filtering the mixture through Celite followed by washing with $CH_2Cl_2$ and being dried with anhydrous $Na_2SO_4$;

removing solvent from the mixture;

purifying residue by silica gel chromatography using petroleum ether and ethyl acetate at 3:1 ratio as an eluent to afford about 73 mg white solid of FA2 in 85% yield;

adding a solution of the FA2 at about 15 mg or 0.038 mmol in about 16 mL of THF with about 1 mL or 0.12 M of LiOH to form a mixture;

stirring the mixture overnight at room temperature under $N_2$ protection to form a reaction solution;

quenching the reaction solution with water and being extracted with ethyl acetate;

drying the combined organic phase with $Na_2SO_4$ followed by evaporation in vacuum;

purifying residue by silica gel chromatography using petroleum ether and ethyl acetate at 1:1 ratio as an eluent to afford about 6 mg white solid of the FA4 in 45% yield.

\* \* \* \* \*